United States Patent [19]

Takayama

[11] Patent Number: 5,123,404
[45] Date of Patent: Jun. 23, 1992

[54] APPARATUS FOR DESTROYING CALCULI

[75] Inventor: Naohiko Takayama, Nagaokakyo, Japan

[73] Assignee: Shimadzu Corporation, Kyoto, Japan

[21] Appl. No.: 583,320

[22] Filed: Sep. 17, 1990

[30] Foreign Application Priority Data

Sep. 27, 1989 [JP] Japan .................................. 1-251394

[51] Int. Cl.$^5$ ............................................. A61B 17/22
[52] U.S. Cl. ........................... 128/24 EL; 128/660.03; 367/155
[58] Field of Search ......... 128/24 EL, 660.03, 661.01, 128/662.04; 73/625, 626; 367/138, 153, 155, 156

[56] References Cited

U.S. PATENT DOCUMENTS

| | | | |
|---|---|---|---|
| 3,513,439 | 5/1970 | Egli | 367/155 |
| 3,859,984 | 6/1975 | Langley | 128/662.04 |
| 3,987,673 | 10/1976 | Hansen | 128/662.04 |
| 4,821,245 | 4/1989 | Riedlinger | 128/24 EL |
| 4,955,366 | 9/1990 | Uchiyama et al. | 128/24 EL |

FOREIGN PATENT DOCUMENTS 0027542 9/1980 European Pat. Off. .
0133946 7/1984 European Pat. Off. .

OTHER PUBLICATIONS

Fry, William, "The Use of Ultrasound in Neurosurgey" Proceedings of the Third International Conference on Medical Electronics, London, 1960.

Primary Examiner—Francis Jaworski
Assistant Examiner—Scott N. Akers
Attorney, Agent, or Firm—Wegner, Cantor, Mueller & Player

[57] ABSTRACT

Apparatus for destroying calculi in a living body by ultrasonic waves, wherein a plurality of ultrasonic transducers are arranged on the plane surface of a supporting member, with their axes being inclined in such a manner that the axes of the ultrasonic beams produced by the transducers meet at a point where a calculus to be destroyed is positioned.

2 Claims, 6 Drawing Sheets

APPARATUS FOR DESTROYING CALCULI

BACKGROUND OF THE INVENTION

This invention relates to an apparatus for destroying calculi in a living body, which comprises means for generating utrasonic waves outside the body and means for causing the waves to converge on a calculus within the body.

As is well known, calculi are formed in such organs of a living body as the kidney or gall-bladder. There are various ways of removing calculi from living organs, such as by conducting a surgical operation, melting them by chemical drugs, or destroying them by ultrasound. If the calculus is too large to be melted by chemicals, surgical operation or application of ultrasound is useful for removal of the calculus. Surgical operation, however, not only gives much pain to the patient but also requires careful aftercare of the patient. Use of ultrasound is advantageous since it suffers little from such difficulties.

As schematically shown in FIG. 2, one known apparatus for destroying calculi by ultrasound comprises a spherical shell 1 and a plurality of piezoelectric elements $2_1$-$2_n$ arranged on the concave inner surface of the spherical shell at whose center the calculus to be destroyed is positioned. When the elements 2 are actuated simultaneously, they produce a beam of ultrasonic waves, and all the beams from the elements are focused on a point F set at the center of the spherical shell 1 to destroy the calculus positioned at the point F. A bag 3 filled with degassed liquid such as water and enclosing the piezoelectric elements is interposed between a patient K and the elements.

Another known device is schematically shown in FIG. 3 comprising a plurality of piezoelectric elements $2_1$-$2_n$ arranged on the flat upper surface of a circular supporting plate 4. The elements are so controlled that the phase of the ultrasonic wave produced by each of the elements coincides with those of the waves produced by the other elements at a point F. A main controller MC produces a series of pulses, which are applied through delay circuits $D_1$-$D_n$ to high-voltage pulse generators $G_1$-$G_n$, each of which actuates the corresponding one of the piezoelectric elements $2_1$-$2_n$ to produce an ultrasonic beam, the delay circuits $D_1$-$D_n$ providing such different delay times that the ultrasonic beams produced by all the piezoelectric elements coincide in phase with each other at the point F so as to destroy a calculus positioned at the point. A bag 3 filled with degassed liquid such as water is interposed between the piezoelectric elements and a patient's body in which a calculus to be crushed is contained.

The arrangement of FIG. 2 has a disadvantage that the whole apparatus is bulky because of the spherical configuration of the shell 1 on which the ultrasonic transducers are arranged, and that it is difficult to make the apparatus of a compact size.

The arrangement of FIG. 3 has an advantage that the piezoelectric elements can be positioned near the body of a patient, thereby to make decrement of the ultrasonic waves caused by divergence less than in the arrangement of FIG. 2. The arrangement of FIG. 3, however, has the following problem. Suppose that a piezoelectric element in the form of a circular plate has a radius of b. As shown in FIG. 4, the ultrasonic beam produced by a piezoelectric element 2 diverges as it advances, and the half angle $\alpha$ of divergence to a zero pressure point is given by $$\sin \alpha = 0.6\lambda/b \quad (1)$$

wherein $\lambda$ is the wavelength of the beam. The radius d of the sectional plane of the ultrasonic beam at the position of a calculus to be destroyed is given by $$d = l \tan \alpha \quad (2)$$

wherein l is the distance between the piezoelectric element and the position of the calculus, and $\alpha$ is the above-mentioned half angle of divergence to a zero pressure point of the beam.

If the radius b of the piezoelectric element is 1 cm and the frequency is 1 MHz, the angle $\alpha$ will be 5°, and if the distance l is 20 cm, the radius d of the section of the beam will be 1.75 cm. In order that the ultrasonic beams produced by the elements in FIG. 3 are focussed on the point F by controlling the phases of the beams, the sectional areas of the beams of all the elements must overlap one another. To make the radius d of the section of each beam at the point F, that is, the position of the calculus sufficiently large to enable phase control of the beams, the piezoelectric elements must have a smaller diameter, so that the number of piezoelectric elements to be provided increases with resulting increase in the number of high-voltage pulse generators and delay circuits to be provided and in the cost of manufacturing the apparatus.

Moreover, there is another disadvantage that due to the directivity of the piezoelectric element, an ultrasonic beam has an intensity distribution in the sectional area thereof, with the intensity becoming weak at the periphery, so that the efficiency at the focal point is reduced.

SUMMARY OF THE INVENTION

The above disadvantages have been overcome by the apparatus of the invention, which comprises a plurality of ultrasonic transducers arranged on one plane surface of a plate-like supporting member in such a manner that the axes of the ultrasonic beams generated by the transducers meet at a focal point a predetermined distance away from the one surface of the supporting member, and means for supporting a living body at such a position that a calculus in the living body coincides with the focal point on which the ultrasonic energies produced by the transducers are concentrated to destroy the calculus.

Since the ultrasonic transducers are provided on a plane surface and so directed that the axes of the ultrasonic beams produced by the transducers cross at a point, the whole apparatus can be made of a compact size, the operability of the apparatus is improved, and the number of high-voltage pulse generators and delay circuits to be provided is reduced thereby to reduce the manufacturing cost of the apparatus, and improve the directivity pattern of the ultrasonic transducers and the efficiency of destruction at the focal point of the ultrasonic beams.

To detect the position of a calculus, an ultrasonic sector or convex transducer may be provided on the supporting member. The former is a diagnostic device provided with an ultrasonic oscillator so arranged as to scan a sector plane area of a living body to be examined thereby to observe the interior of the body at sectional planes, while the latter is a diagnostic device provided with an array of convex oscillators to observe the interior of a living body at sectional planes. Use of such diagnostic devices advantageously makes it possible to locate the position of the calculus to be destroyed within a living body.

In accordance with the invention, there is provided means for controlling the phases of the ultrasonic waves produced by the ultrasonic transducers so that the phases of the waves from all the transducers coincide at the position of the calculus to be destroyed. To control the phases in the above-mentioned manner, delay circuits can advantageously be used to provide different delay times of the order of nanoseconds at which the actuating signal from a main controller is applied to the ultrasonic transducers so that the energies of the ultrasonic waves produced by the transducers are concentrated on the position of the calculus, thereby to increase the destroying power of the waves at the position.

In accordance with the invention, the ultrasonic transducers can comprise a plurality of piezoelectric elements, magnetostriction oscillators, or electromagnetic coils. The piezoelectric element is a transducer composed of a crystal which produces a voltage when it is strained and conversely becomes strained when a voltage is impressed upon it. Ceramics such as $BaTiO_3$, $NaNbO_3$, $KNbO_3$, PbZr, $PbTiO_3$ can be used as a piezoelectric element. The magnetostriction oscillator is an element which becomes strained when subjected to a magnetic field. The electromagnetic coil is a device which comprises a coil and a piece of copper foil provided adjacent the coil with an electrically insulating film interposed therebetween so that electromagnetic induction of the coil causes the copper foil to vibrate thereby to produce ultrasonic waves.

As mentioned above, a plurality of ultrasonic transducers are provided on a plane supporting member and so arranged that the axes of the ultrasonic beams produced by the elements meet at a focal point spaced a predetermined distance away from the supporting member, where the energies of the ultrasonic waves are concentrated to destroy a culculus positioned at the focal point. The arrangement makes the whole apparatus compact, decreases the number of high-voltage pulse generators and delay circuits to be provided thereby to reduce the manufacturing cost of the apparatus, and improves the directivity pattern of the ultrasonic transducers and the efficiency of destruction at the focal point of the beams.

In the prior art arrangement of FIG. 2, suppose that the spherical shell 1 for holding the ultrasonic transducers has a diameter D of 30 cm and the distance l between the focal point F and the transducers on the shell 1 is 26 cm. The height H of the shell is 5 cm as shown in FIG. 5. In the arrangement of the present invention, the plate-like supporting member has a thickness smaller than the above height H of the shell in the prior art arrangement, so that the whole apparatus can be made the more compact.

As compared with the prior art arrangement of FIG. 3, in accordance with the invention, the ultrasonic transducers can have a larger diameter, so that the number of high-voltage generators and delay circuits to be provided and consequently the manufacturing cost of the apparatus can be reduced.

In the prior art arrangement of FIG. 3, suppose that the diameter D of the supporting disk is 30 cm, that the distance l between the center of the supporting disk 1 and the focal point F of the ultrasonic beams from the transducers is 25 cm, and that the frequency of the ultrasonic waves is 1 MHz. As shown in FIG. 6, the angle $\alpha'$ that the line A' connecting the point F and the center of an ultrasonic transducer 2 on the periphery of the supporting disk 1 makes with the axis A of the transducer is given by $$\alpha' = \tan^{-1}(15/25) = 30°$$

As previously mentioned, the half angle $\alpha$ of divergence to a zero pressure point of the ultrasonic beam from an ultrasonic transducer is given by $$\sin \alpha = 0.6\lambda/b$$

Then, $$b = 0.6\lambda/\sin \alpha$$

In order that the pressure of the ultrasonic beam produced by the transducer on the periphery of the supporting disk 1 will not become zero at the point F, the radius b of the transducer must be smaller than $0.6\lambda/\sin \alpha'$, that is, $0.6 \times 0.15$ cm/sin $30° = 0.18$ cm. The surface area of a circular transducer having a radius of 0.18 cm is $0.18^2\pi$ cm$^2$, so that about 7000 transducers are required to occupy the surface area ($15^2\pi$ cm$^2$) of the supporting disk having a diameter of 30 cm. The number is too great for practical use.

In accordance with the invention, it is possible to use transducers having a larger diameter, and if transducers having a diameter of 2 cm are used, about 220 transducers suffice to cover the surface area of a supporting plate having a diameter of 30 cm.

Each of the transducers may be provided at one surface thereof with an acoustic lens so that the ultrasonic beams from the transducers are focused at a point.

DETAILED DESCRIPTION OF A PREFERRED EMBODIMENT

A preferred embodiment of the invention will be described in detail with reference to the drawings.

Figure 1:
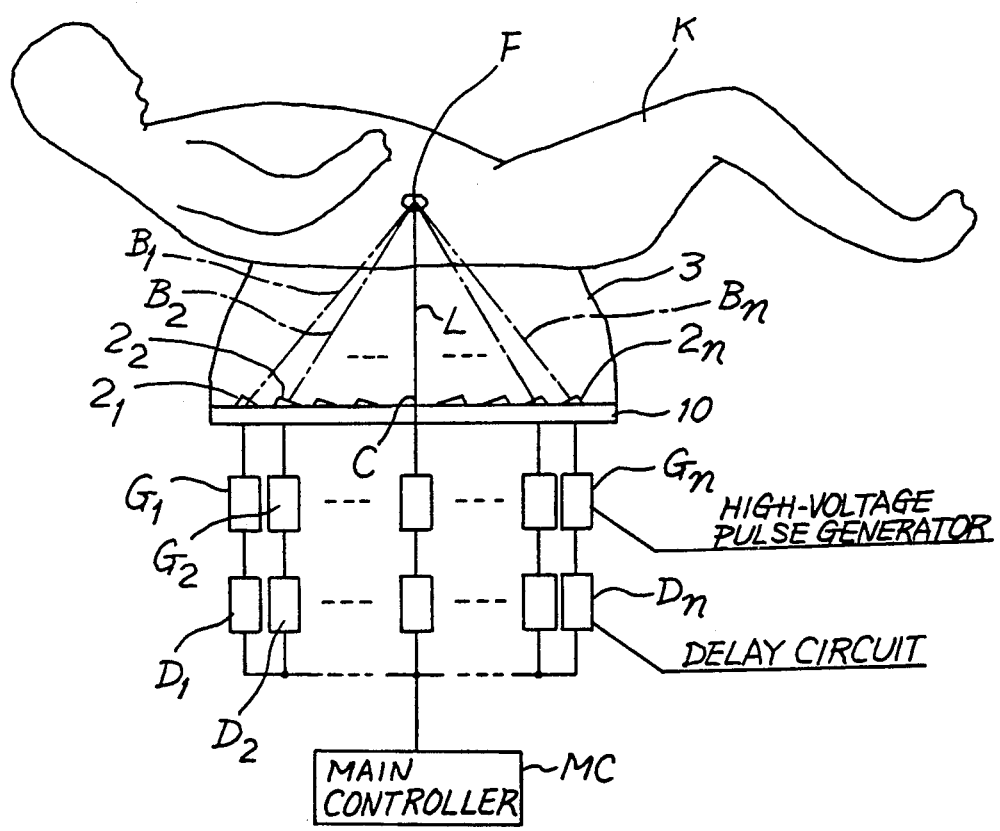
FIG. 1 is a schematic side view of one embodiment of the invention.
Figure 2:
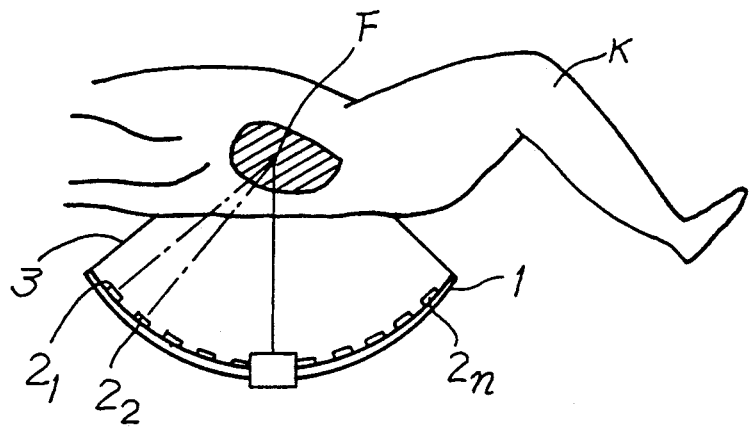
FIG. 2 is a schematic side view of a known apparatus for destroying calculi.
Figure 3:
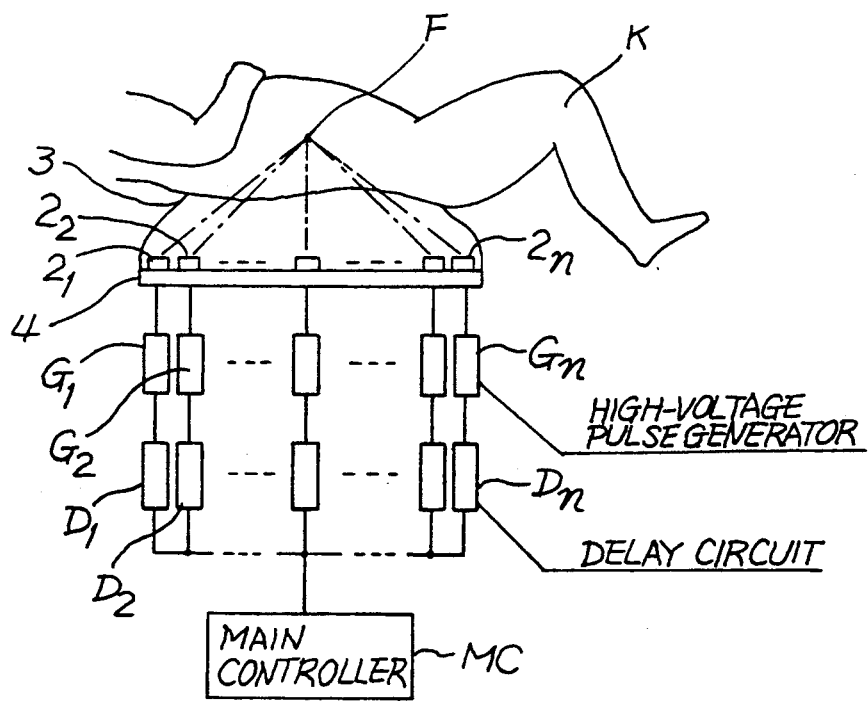
FIG. 3 is a schematic side view of another known apparatus for destroying calculi.
Figure 4:
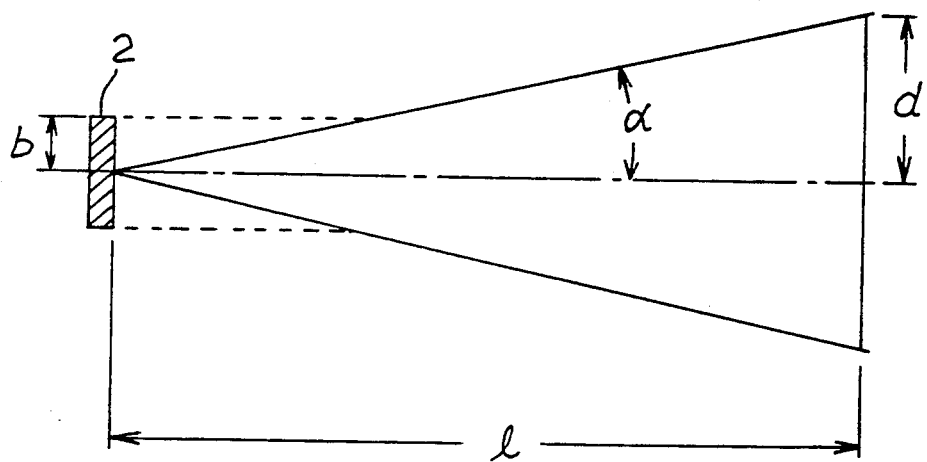
FIG. 4 is a schematic side view of an ultrasonic transducer, with an ultrasonic beam emitted by the transducer.
Figure 7:
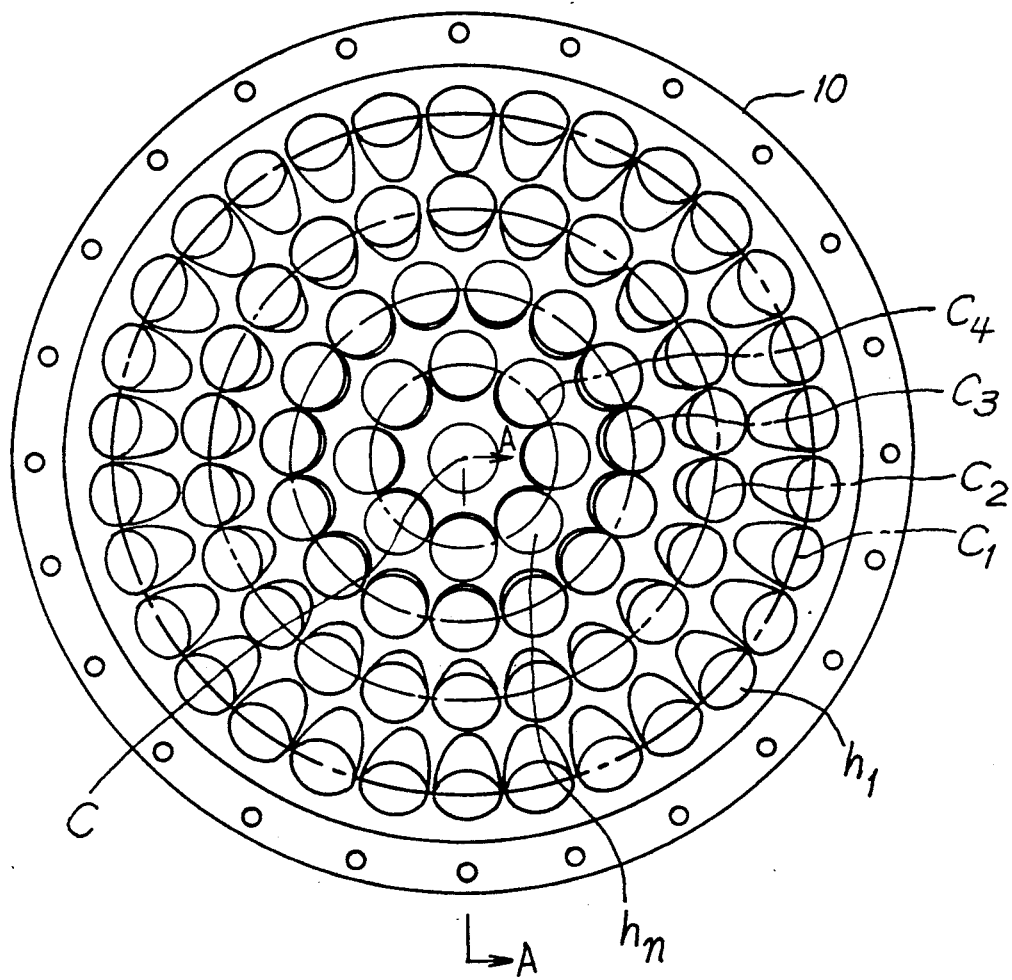
FIG. 7 is a top plan view of a plate for supporting ultrasonic transducers used in one embodiment of the invention.
Figure 8:
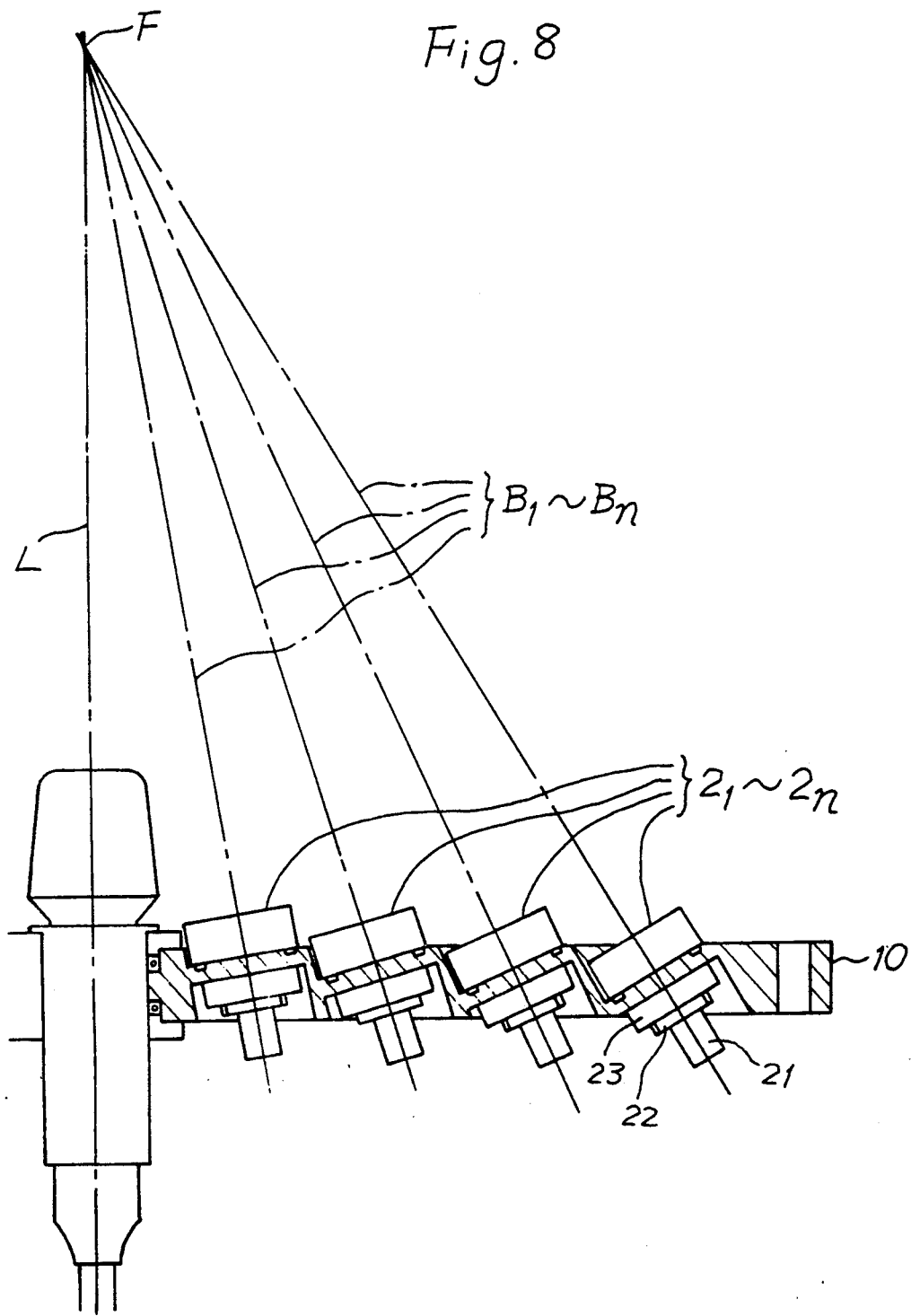
FIG. 8 is a sectional view taken along line A—A in FIG. 7.

There is schematically shown in FIG. 1 a disk-like supporting member 10, on the upper face of which a plurality of piezoelectric elements $2_1$-$2_n$ are mounted in such a manner that the axes $B_1$-$B_n$ of the ultrasonic beams produced by the elements $2_1$-$2_n$ meet at a point F a predetermined distance away from the center C of the supporting member 10 so that the energies of the beams are concentrated on the point F. As shown in detail in FIG. 7, the disk-like supporting member 10 is provided with a plurality of holes $h_1$-$h_n$ formed along the circumferences of a plurality, say, four concentric circles $C_1$, $C_2$, $C_3$ and $C_4$ about the center C of the supporting member 10. The piezoelectric elements $2_1$-$2_n$ are fitted in the holes $h_1$-$h_n$, respectively. In the following description when reference is made in general to the component parts of the apparatus such as the piezoelectric elements $2_1$-$2_n$, the axes $B_1$-$B_n$ of the ultrasonic beams, or the holes $h_1$-$h_n$ will be designated by only the reference numerals or symbols without the suffixes.

The holes h are formed in such a manner that the piezoelectric elements 2 fitted in the holes h have thier axes so inclined as to meet at a point F on a perpendicular line L passing the center C of the supporting member 10 and spaced a predetermined distance away from the center C. The axes of the elements 2 in the holes h along an outer one of the circles $C_1$-$C_4$ are more inclined than those in the holes h along the inner circles.

Figure 9:
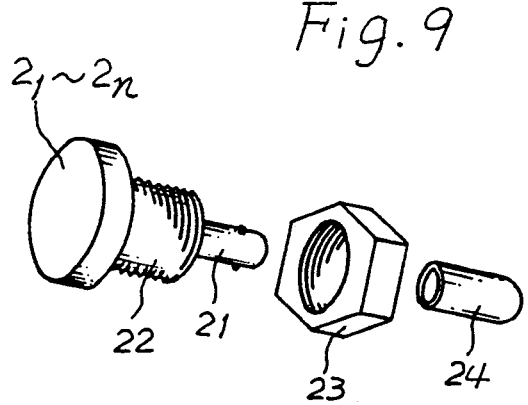
FIG. 9 is an exploded, perspective view of an ultrasonic transducer with a fixing nut and an electrical connector.
Figure 6:
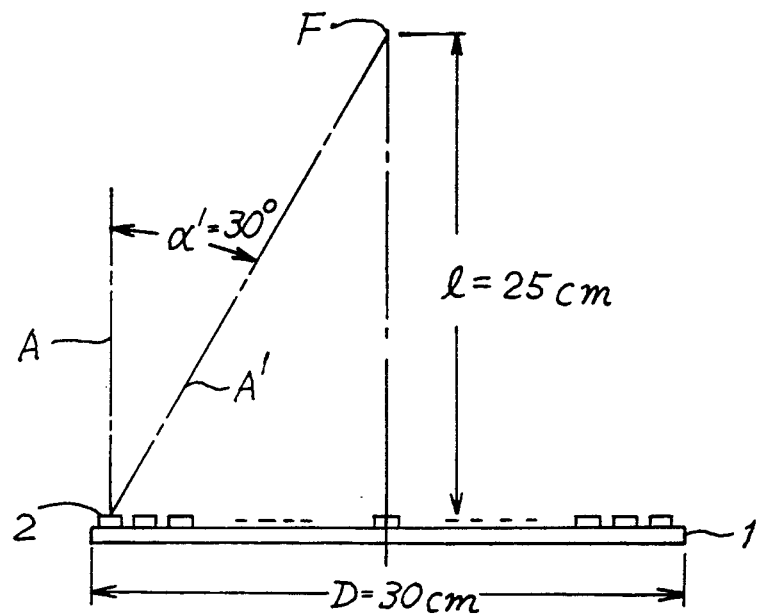
FIG. 6 is a schematic side view showing the dimensions of the apparatus of FIG. 3.
Figure 5:
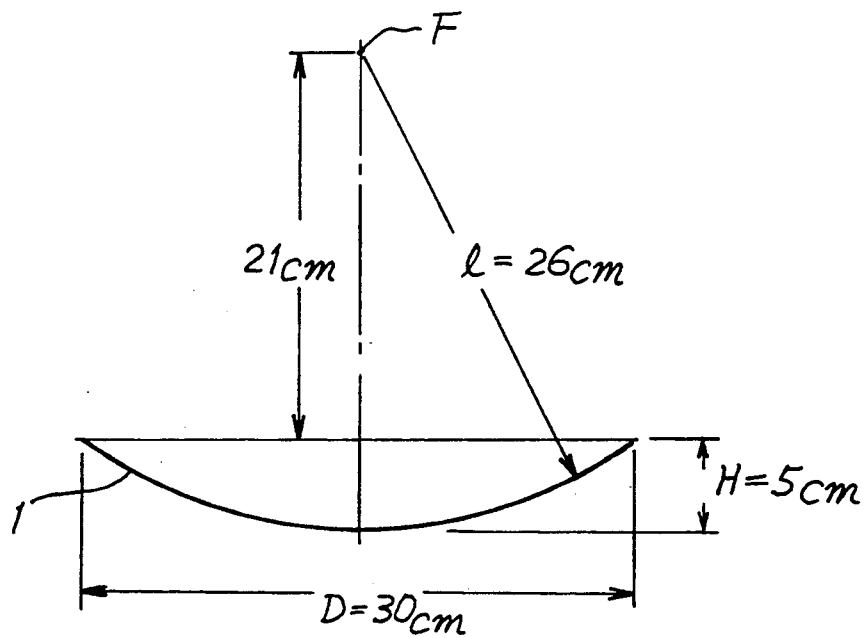
FIG. 5 is a schematic side view showing the dimensions of the apparatus of FIG. 2.

As shown in detail in FIG. 9, each of the piezoelectric elements 2 has a leg 21 externally threaded as at 22, and is fitted in one of the holes h by inserting its leg therethrough, with a nut 23 threaded on the external thread 22 of the leg 21. A connector 24 is fixed to the leg 21 for connection to an electric circuit to be described hereinafter.

A bag 3 filled with degassed liquid such as water is provided on the supporting member 10 to enclose the piezoelectric elements 2 therein. A patient K to be treated lies on the bag 3 so that the water in the bag is interposed between the piezoelectric elements 2 and the patient's body.

A main controller MC produces a series of electric pulses, which are applied through delay circuits $D_1$-$D_n$ to high-voltage pulse generators $G_1$-$G_n$, respectively. The pulses produced by the generators $G_1$-$G_n$ are applied through the connectors 24 to the piezoelectric elements $2_1$-$2_n$, respectively, each of which produces a beam of ultrasonic waves. As previously mentioned, the axes $B_1$-$B_n$ of the beams from all the piezoelectric elements meet at the point F. The delay circuits provide such different delay times as to cause the phases of the ultrasonic waves from all the piezoelectric elements to coincide at the point F, thereby to increase the ultrasonic energy concentrated on the point F, so that it is possible to destroy the calculus positioned at the point F efficiently and accurately.

As previously mentioned, instead of the piezoelectric elements other ultrasonic transducers such as magnetostriction oscillators or electromagnetic coils may also be used.

By changing the delay constant of the delay circuits it is possible to change the focal point of the ultrasonic beams as the position of the calculus to be destroyed changes. The apparatus of the invention may also be easily used in combination with fluoroscopy.

What I claim is:

1. Apparatus for destroying calculi in a living body, comprising:
   a) a plurality of ultrasonic transducers;
   b) actuating means for actuating said ultrasonic transducers to produce beams of ultrasonic waves;
   c) supporting means for supporting said ultrasonic transducers plate with their axes inclined in such a manner that the axes of said ultrasonic beams meet at a focal point spaced a predetermined distance away from said supporting means so that energy from said ultrasonic beams is concentrated at the focal point, wherein said supporting means comprises a plate-like member recesses to provide a plurality of holes, in each of which one of said ultrasonic transducers is fitted, each of said recesses having a bottom face which is so inclined that the axes of said ultrasonic beams produced by all said transducers meet at said focal point when said transducers are supported in said recesses; and
   d) liquid-containing means for supporting said living body above said ultrasonic transducers so that a calculus in said living body may be positioned at said focal point;

wherein said actuating means comprises:
   a plurality of high-voltage pulse generators each connected to one of said ultrasonic transducers;
   a main controller for producing a series of pulses; and
   a plurality of delay circuits each connected between said main controller and one of said high-voltage pulse generators, said delay circuits providing different delay times such that said series of pulses produced by said main controller cause said high-voltage pulse generators to actuate said ultrasonic transducers in such a manner that the phases of the ultrasonic waves produced by said ultrasonic transducers coincide at said focal point.

2. The apparatus of claim 1, wherein each of said ultrasonic transducers consists of one of a piezoelectric element, a magnetostriction oscillator and an electromagnetic coil combined with a metal foil.

* * * * *